US00PP21044P2

(12) United States Plant Patent
Hartman

(10) Patent No.: US PP21,044 P2
(45) Date of Patent: Jun. 1, 2010

(54) ***CALADIUM* PLANT NAMED 'WHITE WONDER'**

(50) Latin Name: *Caladium×hortulanum*
Varietal Denomination: White Wonder

(76) Inventor: Robert Dale Hartman, 158 Blue Moon Ave., Lake Placid, FL (US) 33852

( * ) Notice: Subject to any disclaimer, the term of this patent is extended or adjusted under 35 U.S.C. 154(b) by 0 days.

(21) Appl. No.: 12/321,740

(22) Filed: Jan. 23, 2009

(51) Int. Cl.
*A01H 5/00* (2006.01)

(52) U.S. Cl. ..... Plt./373
(58) Field of Classification Search ..... Plt./373, Plt./263.1
See application file for complete search history.

*Primary Examiner*—Kent L Bell
(74) *Attorney, Agent, or Firm*—C. A. Whealy

(57) ABSTRACT

A new and distinct cultivar of *Caladium* plant named 'White Wonder', characterized by its intermediate plant habit; vigorous and dense growth habit; rapid growth rate; and strap-type leaves that are white to grey-green in color with light pink to white-colored veins and dark green-colored borders.

4 Drawing Sheets

Botanical designation: *Caladium×hortulanum.*
Cultivar denomination: 'WHITE WONDER'.

BACKGROUND OF THE INVENTION

The present invention relates to a new and distinct cultivar of *Caladium* plant, botanically known as *Caladium×hortulanum,* commercially referred to as a strap leaf-type *Caladium* and hereinafter referred to by the name 'White Wonder'.

The objective of the Inventor's breeding program is to create new *Caladium* cultivars that have uniform plant habit, exceptional performance and attractive foliage coloration.

The new *Caladium* plant originated from a self-pollination made by the Inventor in April, 2002, in Lake Placid, Fla. of *Caladium×hortulanum* 'White Wing', not patented. The new *Caladium* plant was discovered and selected by the Inventor as a single plant within the progeny of the stated self-pollination in a controlled outdoor nursery environment in Lake Placid, Fla. on Jun. 15, 2003.

Asexual reproduction of the new *Caladium* plant by tuber divisions in a controlled outdoor nursery environment in Lake Placid, Fla. since Apr. 15, 2004 has shown that the unique features of this new *Caladium* plant are stable and reproduced true to type in successive generations of asexual reproduction.

SUMMARY OF THE INVENTION

Plants of the new *Caladium* have not been observed under all possible environmental conditions. The phenotype may vary somewhat with variations in environment such as temperature and light intensity, without, however, any variance in genotype.

The following traits have been repeatedly observed and are determined to be the unique characteristics of 'White Wonder'. These characteristics in combination distinguish 'White Wonder' as a new and distinct cultivar of *Caladium:*

1. Intermediate plant habit.
2. Vigorous and dense growth habit; rapid growth rate.
3. Strap-type leaves that are white to grey-green in color with light pink to white-colored veins and dark green-colored borders.

Plants of the new *Caladium* differ from plants of the parent, 'White Wing', in the following characteristics:

1. Plants of the new *Caladium* are more compact and denser than plants of 'White Wing'.
2. Plants of the new *Caladium* grow faster than plants of 'White Wing'.
3. Leaves of plants of the new *Caladium* are more rounded than and not as pointed as leaves of plants of 'White Wing'.
4. Plants of the new *Caladium* and 'White Wing' differ in leaf coloration as plants of 'White Wing' have white-colored leaves with a mottled dark and light green-colored borders.

Plants of the new *Caladium* can be compared to plants of 'Candidum Junior', not patented. In side-by-side comparisons conducted in Lake Placid, Fla., plants of the new *Caladium* differed primarily from plants of 'Candidum Junior' in the following characteristics:

1. Plants of the new *Caladium* had strap-type leaves whereas plants of 'Candidum Junior' had fancy-type leaves.
2. Plants of the new *Caladium* and 'Candidum Junior' differed in leaf coloration as plants of 'Candidum Junior' had white-colored leaves with green-colored venation and narrow green-colored borders.

Plants of the new *Caladium* can be compared to plants of 'Florida White Ruffles', disclosed in U.S. Plant Pat. No. 14,402. In side-by-side comparisons conducted in Lake Placid, Fla., plants of the new *Caladium* differed primarily from plants of 'Florida White Ruffles' in the following characteristics:

1. Plants of the new *Caladium* were more upright than plants of 'Florida White Ruffles'.
2. Plants of the new *Caladium* and 'Florida White Ruffles' differed in leaf coloration as plants of 'Florida White Ruffles' had creamy white-colored leaves with creamy white-colored venation and green-colored borders.

BRIEF DESCRIPTION OF THE PHOTOGRAPHS

The accompanying photographs illustrate the overall appearance of the new *Caladium.* These photographs show the colors as true as it is reasonably possible to obtain in colored reproductions of this type. Colors in the photographs may differ slightly from the color values cited in the detailed botanical description which accurately describe the colors of the new *Caladium*.

The photograph on the first sheet is a side perspective view of a typical plant of 'White Wonder' grown in a container in a shadehouse.

The photograph at the top of the second sheet is a side perspective view of typical plants of 'White Wonder' (top center), 'Candidum Junior' (left) and 'Florida White Ruffles' (right) grown in a shadehouse.

The photograph at the bottom of the second sheet is a side perspective view of typical plants of 'White Wing' (left) and 'White Wonder' (right) grown in a shadehouse.

The photograph at the top of the third sheet is a top perspective view of typical plants of 'White Wonder' grown in an outdoor nursery.

The photograph at the bottom of the third sheet is a close-up view of typical freshly-dug tubers and roots of 'White Wonder'.

The photograph on the fourth sheet is a close-up view of a typical inflorescence of 'White Wonder'.

DETAILED BOTANICAL DESCRIPTION

The aforementioned photographs and following observations and measurements describe plants grown in 15-cm containers in Avon Park, Fla. during the summer in a polypropylene-covered shadehouse and plants grown in ground beds in Zolfo Springs, Fla. during the late summer in an outdoor nursery. All plants were grown under conditions and practices which approximate those generally used in commercial *Caladium* production. During the production of the plants, day temperatures ranged from about 29° C. to 35° C., night temperatures ranged from about 22° C. to 26° C. and light levels were about 8,000 foot-candles (shadehouse) or 10,000 to 12,000 foot-candles (outdoor nursery). Plants had been growing in the shadehouse for five weeks from planting tubers when the photographs and the detailed description were taken. Plants had been growing in the outdoor nursery for seven months from planting tuber pieces when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'White Wonder'.

Parentage:

*Female, or seed, parent.*—*Caladium×hortulanum* 'White Wing', not patented.

*Male, or pollen, parent.*—*Caladium×hortulanum* 'White Wing', not patented.

Propagation:

*Type.*—By tubers and by tuber divisions.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented; individual segments ovate in shape. Height: About 4 cm. Diameter: About 5.2 cm. Texture: Thick, starchy; somewhat brittle. Color: Epidermis, between 199A and 165C to 165D; interior, close to 2D. Root description: Dense, thick, fleshy; white, close to 155C, in color.

Plant description:

*Plant type.*—Herbaceous perennial.

*Plant/growth habit.*—Upright and intermediate plant habit; inverted triangle; rapid growth rate; vigorous, dense growth habit; suitable for 15-cm to 25-cm containers. Leaf petioles arising from tubers; petioles mostly upright and leaning outwardly with development.

*Plant height, from soil level to top of leaf plane, shadehouse-grown plants.*—About 33 cm to 38 cm.

*Plant height, from soil level to top of inflorescences, shadehouse-grown plants.*—About 46.3 cm.

*Plant diameter or spread, shadehouse-grown plants.*—About 47 cm to 53 cm.

*Cataphylls* (*only observed on shadehouse-grown plants*).—Length: About 7.5 cm. Width: About 1.1 cm. Shape: Lanceolate. Apex: Acute to cuspidate. Base: Sheathing the stem. Color, inner and outer surfaces: Between 161D and 159B to 159C often tinged with close to 181D and streaked with close to 200B to 200C; with development, color becoming closer to 200C.

Foliage description:

*Length, shadehouse-grown plants.*—About 19 cm to 23.5 cm.

*Width, shadehouse-grown plants* (*flattened*).—About 12 cm to 16.5 cm.

*Shape.*—Ovate.

*Apex.*—Acuminate.

*Base.*—Sagittate-peltate to sagittate.

*Margin.*—Entire; undulate.

*Texture, upper surface.*—Smooth, glabrous.

*Texture, lower surface.*—Smooth, glabrous; glaucous.

*Venation pattern.*—Pinnate.

*Color, shadehouse-grown plants.*—Developing leaves, upper surface: Center: Between 155C and 192D; random diffuse areas, close to 137A; basal notch, close to between 187C and 59A to 59B. Border and margins: Close to 147A; random diffuse areas, close to 137A. Venation: Midrib, close to 192B; lateral veins, close to 192A to 192B. Developing leaves, lower surface: Center: Close to 155C; random diffuse areas, close to 147B to 147C; basal notch, close to 59A to 59B. Border and margins: Between 147B and 191A; faint and thin marginal edge, close to 187B. Venation: Midrib, distal, close to 147D and proximal, close to 158D; lateral veins, close to 147C to 147D tinged with close to 182D. Fully expanded leaves, upper surface: Center: Close to 155C; random diffuse areas, close to 147A or 191C; basal notch, close to 187B to 187D; occasionally with random spots/streaks, close to 185D. Border and margins: Close to 147A; thin marginal band, close to 187B. Venation: Midrib, close to 155A to 155B; distal lateral veins, close to 192D; proximal lateral veins, close to 155B with adjacent speckles, close to 138A. Fully expanded leaves, lower surface: Center: Close to 155C; random diffuse areas, close to 147B to 147B; basal notch, close to 187B; occasionally with random spots/streaks, close to 186C to 186D. Border and margins: Between 191A and 147B; thin marginal band, close to 187B. Venation: Midrib, distal, close to 147C; midrib, proximal, close to 159C faintly tinged with close to 182D; distal lateral veins, close to 147C with adjacent speckles, close to 138B; proximal lateral veins, close to 147C tinted with close to 182D.

*Petiole.*—Aspect: Mostly erect, leaning outwardly with development. Length, shadehouse-grown plants: About 28 to 35 cm. Diameter, distal, shadehouse-grown plants: About 4 mm. Diameter, proximal, shadehouse-grown plants: About 9.5 mm. Color, proximal, shadehouse-grown plants: Between 161D and 159B to 159C often tinged with close to 181D and boldly striped with between 200B to 200C and N200A. Color, distal, shadehouse-grown plants: Between 161D and 159B to 159C streaked with between 200B to 200C and N200A. Wing length, shadehouse-grown plants: About 8 cm. Wing diameter, shadehouse-grown plants: About 8 mm. Wing color, shadehouse-grown plants: Between 161 D and 159B to 159C often tinged with close to 181D and boldly striped or streaked with between 200B to 200C and N200A.

Inflorescence description: Inflorescences only observed on shadehouse-grown plants.

*Inflorescence arrangement.*—Upright hooded spathes surrounding a columnar spadix borne on a tall upright scape. Spadix with sessile, simple female and male flowers separated into two zones. Female flowers arranged on the lower one-third of the spadix; male flowers arranged on the upper two-thirds of the spadix. Sterile flowers develop between female and male flower zones; near this area, the spathe constricts surrounding the female flowers.

*Fragrance.*—None detected.

*Natural flowering season/longevity.*—Plants of the new *Caladium* typically flower during the spring or early summer in central Florida. Flowers develop about four weeks after growth commences. Inflorescences last about three days before fading; inflorescences persistent.

*Spathe.*—Length: About 13 cm. Width, distal: About 4.9 cm. Width, proximal: About 2.8 cm. Width, at constriction: About 8 mm. Shape: Ovate. Apex: Acute to acuminate. Base: Tapering. Margin: Entire; slightly reflexed. Texture, upper and lower surfaces: Smooth, glabrous. Color: Front surface: Upper two-thirds: Close to 155D tinged with close to 145D; color becoming closer to 199C to 199D with development. Lower one-third: Close to 139D; towards the base, deeply colored with close to N186C; color becoming closer to between 191A to 191B and 146B variably streaked with close to 148D with development. Rear surface: Upper two-thirds: Between 145C to 145D and 155A. Lower one-third: Between 191A to 191B and 146B variably streaked with close to 148D. Spadix: Length, entire spadix: About 8.1 cm. Length, male flower zone: About 5.1 cm. Length, sterile flower zone: About 1 cm. Length, female flower zone: About 2 cm. Diameter, male flower zone: About 1.1 cm. Diameter, sterile flower zone: About 6.5 mm. Diameter, female flower zone: About 1.1 cm. Shape: Spindle-shaped to columnar. Apex: Obtuse. Base: Obtuse. Aspect: Upright. Color, mature, male zone: Close to 158A to 158B. Color, mature, sterile zone: Close to 158A to 158B. Color, mature, female zone: Close to 158B to 158C. Male flowers: Quantity per spadix: About 289. Shape: Obovate. Height: About 2.5 mm. Diameter: About 2 mm. Anther color: Close to 158A to 158B. Amount of pollen: Abundant. Pollen color: Close to 11D. Female flowers: Quantity per spadix: About 316. Shape: Obovate. Height: About 3 mm. Diameter: About 2 mm. Stigma color: Close to 158B to 158C. Ovary color: Close to 159D. Scape: Length: About 34 cm. Diameter: About 7 mm. Strength: Sturdy; flexible. Aspect: Erect. Texture: Smooth, glabrous; glaucous. Color: Proximal: Between 161D and 159B to 159C boldly striped with between 200B to 200C and N200A. Distal: Between 146B and 191A to 191B. Seed and fruit: Seed and fruit development have not been observed on plants of the new *Caladium.*

Disease/pest resistance: Plants of the new *Caladium* have been observed to be somewhat tolerant to *Pythium* root rot and *Xanthomonas* leaf spot. Plants of the new *Caladium* have not been observed to be resistant to pests or other pathogens common to *Caladium.*

Temperature tolerance: Plants of the new *Caladium* have been observed to be tolerant to temperatures ranging from about 7° C. to about 40° C.

It is claimed:

1. A new and distinct *Caladium* plant named 'White Wonder' as illustrated and described.

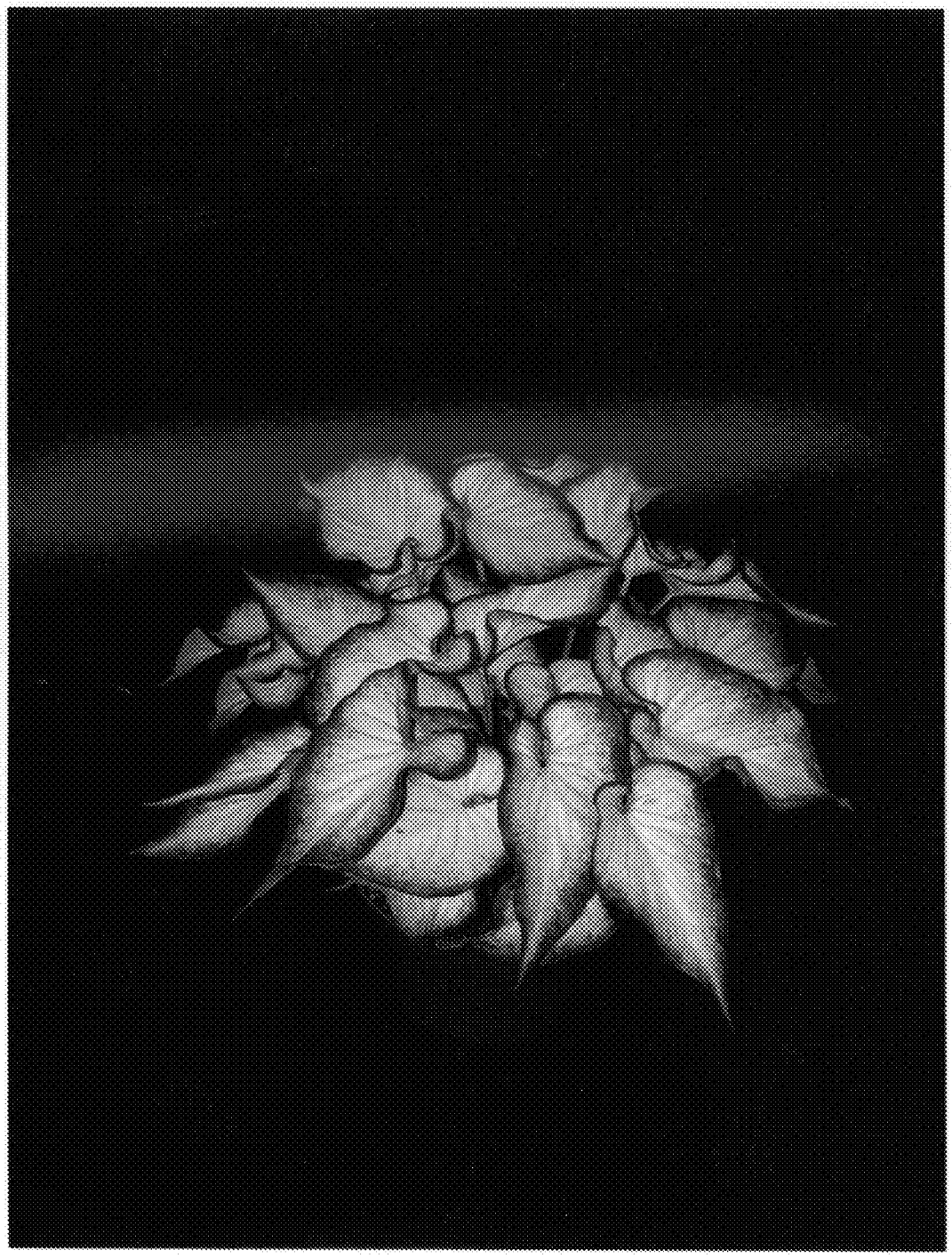

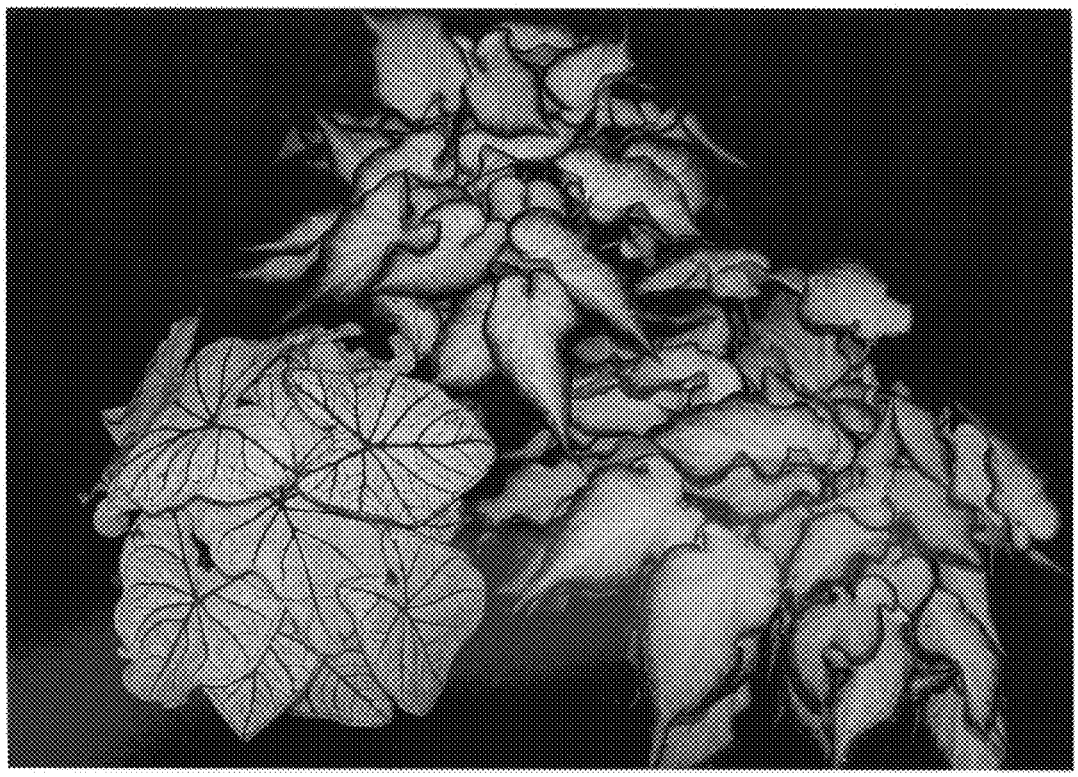
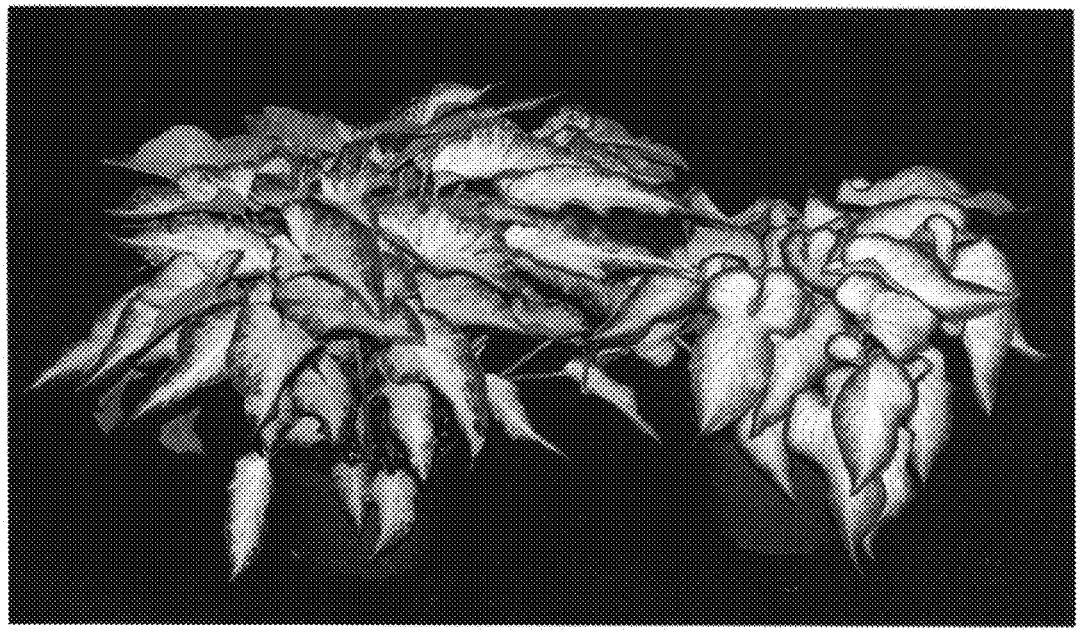

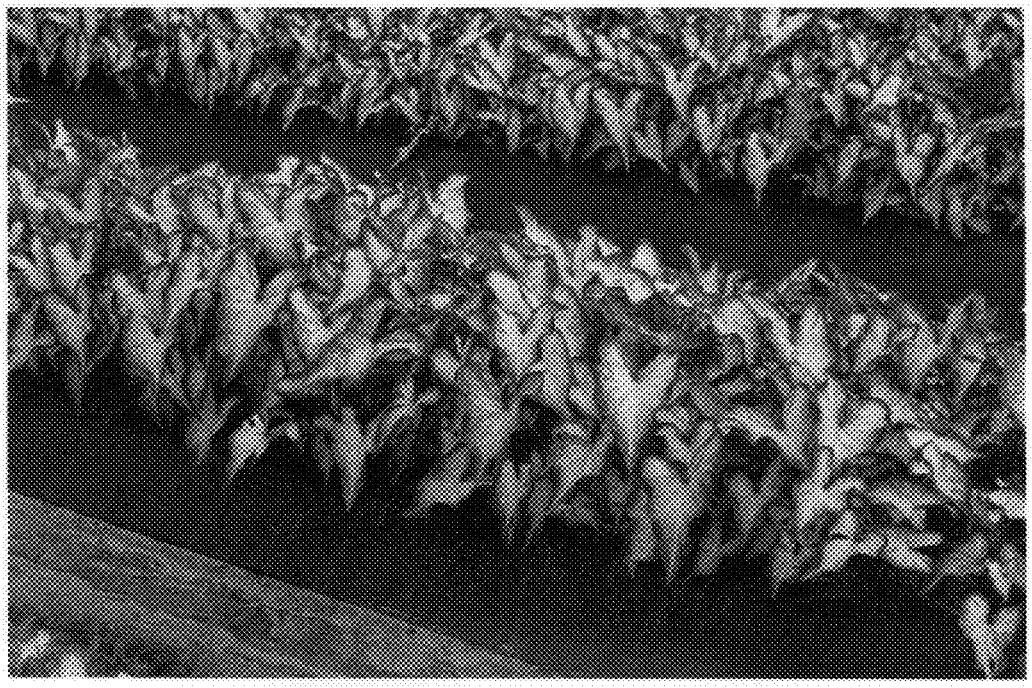
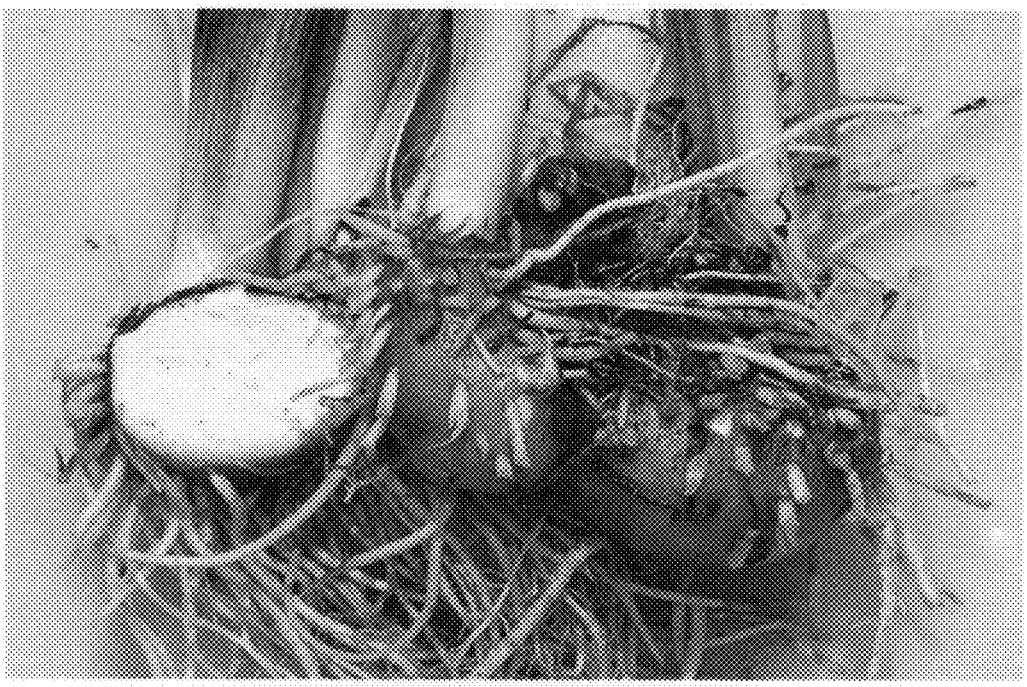

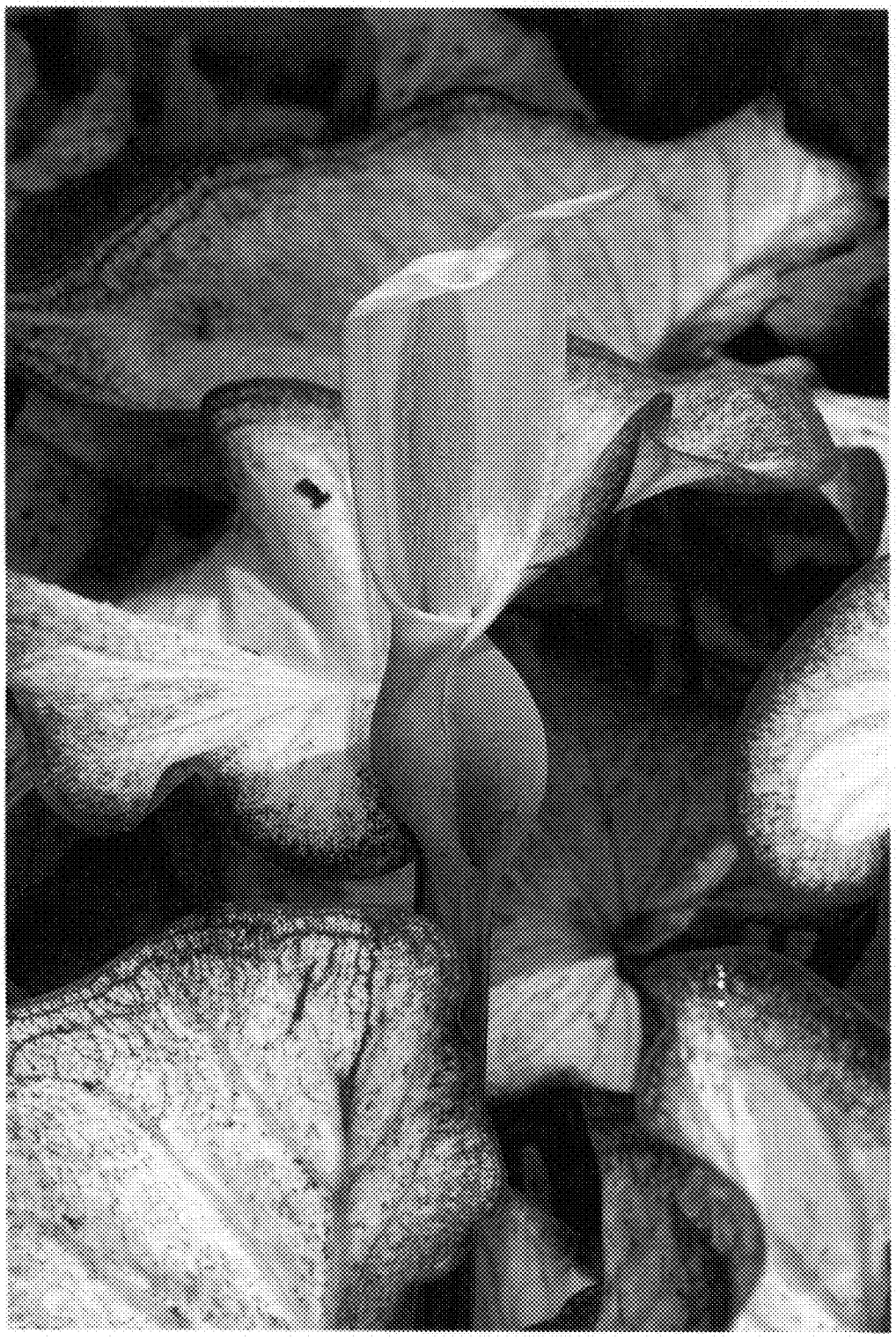

* * * * *